(12) United States Patent
Hurley et al.

(10) Patent No.: US 7,659,233 B2
(45) Date of Patent: *Feb. 9, 2010

(54) PERSONAL CARE COMPOSITIONS WITH SILICONES AND DIHYDROXYPROPYL TRIALKYL AMMONIUM SALTS

(75) Inventors: Megan Kathleen Hurley, Southington, CT (US); Philip Edward Miner, Newtown, CT (US); Stephen Roy Barrow, Trumbull, CT (US); Prem Chandar, Closter, NJ (US); Richard Loren McManus, Shelton, CT (US); Bijan Harichian, Brookfield, CT (US)

(73) Assignee: Conopco, Inc., Englewood Cliffs, NJ (US)

( * ) Notice: Subject to any disclaimer, the term of this patent is extended or adjusted under 35 U.S.C. 154(b) by 578 days.

This patent is subject to a terminal disclaimer.

(21) Appl. No.: 11/222,189

(22) Filed: Sep. 8, 2005

(65) Prior Publication Data

US 2007/0053853 A1    Mar. 8, 2007

Related U.S. Application Data

(63) Continuation-in-part of application No. 10/972,483, filed on Oct. 25, 2004.

(51) Int. Cl.
   *C11D 1/62* (2006.01)
(52) U.S. Cl. .................. 510/130; 510/119; 510/123; 510/504
(58) Field of Classification Search ............ 510/130, 510/119, 123, 504
   See application file for complete search history.

(56) References Cited

U.S. PATENT DOCUMENTS

| | | | |
|---|---|---|---|
| 4,663,159 A | 5/1987 | Brode, II et al. | |
| 4,689,217 A | 8/1987 | Restaino et al. | |
| 4,690,817 A | 9/1987 | Davis et al. | |
| 4,775,715 A | 10/1988 | Beresniewicz et al. | |
| 5,698,183 A | 12/1997 | Langer et al. | |
| 5,773,595 A | 6/1998 | Weuthen et al. | |
| 6,290,978 B2 | 9/2001 | Mak et al. | |
| 6,322,778 B1 * | 11/2001 | Parr et al. | 424/70.28 |
| 6,426,062 B1 * | 7/2002 | Chopra et al. | 424/65 |
| 6,432,907 B1 | 8/2002 | Skold et al. | |
| 6,620,410 B1 | 9/2003 | Cho et al. | |
| 6,649,177 B2 | 11/2003 | Howard et al. | |
| 6,740,317 B1 | 5/2004 | Cho et al. | |
| 6,869,977 B1 | 3/2005 | O'Lenick, Jr. et al. | |
| 7,087,560 B2 * | 8/2006 | McManus et al. | 510/119 |
| 2003/0206933 A1 | 11/2003 | Schulze zue Wiesche et al. | |
| 2003/0211952 A1 | 11/2003 | Erazo-Majewicz et al. | |
| 2004/0156877 A1 | 8/2004 | Tokuyama et al. | |
| 2006/0193805 A1 | 8/2006 | Johnson et al. | |

FOREIGN PATENT DOCUMENTS

| | | |
|---|---|---|
| EP | 1366742 | 12/2003 |
| JP | 63068514 | 3/1988 |
| JP | 1249709 | 10/1989 |
| JP | 9012589 | 1/1997 |
| WO | 00/61066 | 10/2000 |

OTHER PUBLICATIONS

Dow—Quat 188 Cationic Monomer: Overview, Jun. 30, 2004.
Arch Personal Care Products Brochure—Honeyquat 50 Substantive Honey Derivative, Jan. 2004.
Arch Personal Care Products—In vivo study of moisturizing effects of HoneyQuat 50, Jan. 2004.
Cola Moist 200 Brochure—2004.

* cited by examiner

*Primary Examiner*—Anne Marie Grunberg
*Assistant Examiner*—Tracey Simmons Willis

(57) ABSTRACT

A personal care composition is provided with a silicone compound and being aesthetically modified for improved skinfeel with a quaternary ammonium salt, the salt having a structure AB, wherein A is a cationic charged component, B is an anionic charged component, and A has one quaternized nitrogen atom, at least two hydroxyl groups and a molecular weight no higher than about 250.

8 Claims, No Drawings

US 7,659,233 B2

PERSONAL CARE COMPOSITIONS WITH SILICONES AND DIHYDROXYPROPYL TRIALKYL AMMONIUM SALTS

CROSS REFERENCES

This application is a Continuation-In-Part of Ser. No. 10/972,483 filed Oct. 25, 2004.

BACKGROUND OF THE INVENTION

1. Field of the Invention

The invention concerns personal care compositions formulated to impart moisturization and having excellent skinfeel properties.

2. The Related Art

Dry skin is a problem in varying degree to most humans. This condition is particularly evident in winter. Personal care products such as skin creams/lotions, shampoos/conditioners, toilet bars/shower gels and antiperspirants/deodorants are normally formulated with at least one material to address dry skin. Symptoms such as itching, flaking and a visually displeasing dermal appearance can all to some extent be modulated.

There are three traditional classes of materials employed against the problem. Occlusives such as petrolatum or silicone oils serve to inhibit loss of natural moisture. They form a barrier between the epidermis and the environment. Another approach is the use of keratolytic agents to enhance rate of dermal exfoliation. Alpha-hydroxy acids are the most common agents for achieving exfoliation.

A third approach to dry skin is topical application of humectants. Hydroxylated monomeric and polymeric organic substances are generally used for this purpose. Glycerin known also as glycerol is one of the most effective humectants.

Quaternary ammonium compounds have recently been commercialized as moisturizers. One of these known under the trademark Honeyquat 50 with INCI name of Hydroxypropyltrimonium Honey has been reported to be a better humectant than glycerin at levels of 2%. See the Arch/Brooks brochure titled "Cosmetic Ingredients & Ideas®", Issue No. 2, August 2001. Honeyquat 50 is described as being derived from the reaction of pendent hydroxyl groups (on the disaccharide) of a "light" deodorized grade of honey with a chlorohydroxytrimethylammonium derivative. Another commercial quaternary ammonium moisturizer is Cola™ Moist 200 with INCI name of Hydroxypropyl Bis-Hydroxyethyldimonium Chloride. See the Colonial Chemical Inc. brochure titled "Cola™ Moist 200", copyright 2004. U.S. Pat. No. 6,869,977 B1 (O'Lenick, Jr. et al.) to Colonial Chemical Inc. discloses a related monocationic material described as a moisturizing agent.

Many moisturizing actives impart to their formulas an aesthetically displeasing tack and/or sticky skinfeel. The present invention sought to provide a silicone containing moisturizing personal care composition having consumer pleasing skinfeel properties.

SUMMARY OF THE INVENTION

A personal care composition is provided which includes:
(i) from about 0.05% to about 30% by weight of a dihydroxypropyl quaternary ammonium salt of structure AB,
wherein A is a cationic charged component of the salt AB,
B is an anionic charged component of the salt AB, and
A has a single quaternized nitrogen atom, at least two hydroxy groups and a molecular weight no higher than about 250;
(ii) from about 0.05 to about 50% by weight of a silicone.

DETAILED DESCRIPTION OF THE INVENTION

Now it has been found that the skinfeel properties of moisturizing silicone compositions can be improved through inclusion of dihydroxypropyl quaternary ammonium salts as detackifying agents.

Thus, an important material of the present invention is dihydroxypropyl quaternary ammonium salts of structure AB, wherein A is a cationic charged component of the salt AB, and B is an anionic charged component of the salt AB, A has one quaternized nitrogen atom, at least two hydroxyl groups and a molecular weight no higher than about 250 but preferably no higher than about 200, and optimally no higher than 170.

Anionic charged component B may be organic or inorganic with proviso that the material is cosmetically acceptable. Typical inorganic anions are halides, sulfates, phosphates, nitrates and borates. Most preferred are the halides, especially chloride. Organic anionic counter ions include methosulfate, toluoyl sulfate, acetate, citrate, tartrate, lactate, gluconate, and benzenesulfonate. The number and charge of negatively charged component B will be sufficient to neutralize the positive charge of component A.

A preferred embodiment of the quaternary ammonium salts is the dihydroxypropyl tri($C_1$-$C_3$ alkyl or hydroxyalkyl) ammonium salts.

These salts may be obtained in a variety of synthetic procedures, most particularly by hydrolysis of chlorohydroxypropyltri($C_1$-$C_3$ alkyl or hydroxyalkyl)ammonium salts. Ordinarily the $C_1$-$C_3$ alkyl or hydroxyalkyl constituent on the quaternized ammonium group will be methyl, ethyl, n-propyl, isopropyl, hydroxyethyl, hydroxymethyl and mixtures thereof. Particularly preferred is a trimethyl ammonium group known through INCI nomenclature as a "trimonium" group. A most preferred species is 1,2-dihydroxypropyltrimonium chloride, wherein the $C_1$-$C_3$ alkyl is a methyl group.

Another useful species of the quaternary ammonium salts is the material of structure (I).

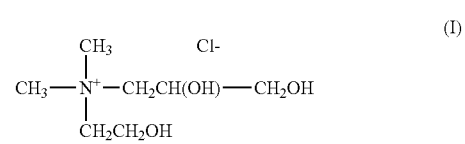

Amounts of the quaternary ammonium salts may range from about 0.05 to about 30%, preferably from about 0.1 to about 25%, more preferably from about 5 to about 20%, optimally from about 10 to about 15% by weight of the composition.

The moisturizing compositions of this invention will include a silicone. A wide variety of silicones including materials of liquid, solid or semi-solid consistency at room temperature can be useful for this invention. Liquid silicones include silicone oils which may be divided into the volatile and nonvolatile variety. The term "volatile" as used herein refers to those materials which have a measurable vapor pressure at ambient temperature. Volatile silicone oils are preferably chosen from cyclic (cyclomethicone) or linear polydimethylsiloxanes containing from 3 to 9, preferably from 4 to 5, silicon atoms. Commercially available volatile silicone oils include DC 200, DC 244, DC 245, DC 344 and DC 345, all supplied by the Dow Corning Corporation; SF-1204, SF-1202 Silicone Fluids, GE 7207 and GE 7158 sourced from GE Silicones; and SWS-03314 sourced from SWS Silicones Corporation.

Useful nonvolatile silicone oils include polyalkyl siloxanes, polyalkylaryl siloxanes and polyether siloxane copolymers. The essentially nonvolatile polyalkyl siloxanes useful herein include, for example, polydimethyl siloxanes with viscosities of from about $5\times10^{-6}$ to 0.1 m$^2$/s at 25° C. Among the preferred nonvolatile emollients useful in the present compositions are the polydimethyl siloxanes having viscosities from about $1\times10^{-5}$ to about $4\times10^{-4}$ m$^2$/s at 25° C. Representative commercial materials include polyalkyl siloxanes sold under the Viscasil Series from G.E. Silicones, and the DC 200 series sold by the Dow Corning Corporation. Polyalkylaryl siloxanes including polymethylphenyl siloxanes such as SF 1075 methyl-phenyl fluid and 556 Cosmetic Grade Fluid (sold by Dow Corning Corporation) may also be useful. Illustrative polyoxyalkylene ether copolymers are commercially available as SF 1066 from G.E. Silicones, and PEG-10 Dimethicone available from Shin-Etsu.

Another class of nonvolatile silicones are emulsifying and non-emulsifying silicone elastomers. Representative of this category is Dimethicone/Vinyl Dimethicone Crosspolymer available as Dow Corning 9040, General Electric SFE 839, and Shin-Etsu KSG-18. Silicone waxes such as Silwax WS-L (Dimethicone Copolyol Laurate) may also be useful.

Amounts of the silicone may range from about 0.05 to bout 50%, preferably from about 0.5 to about 40%, more preferably from about 2 to about 20%, optimally from about 5 to about 12% by weight of the composition.

Emollient materials may serve as cosmetically acceptable carriers. These may be in the form of natural or synthetic esters and hydrocarbons. Amounts of the emollients may range anywhere from about 0.1 to about 60%, preferably between about 1 and about 30% by weight of the composition.

Among the ester emollients are:

(a) Alkyl esters of saturated fatty acids having 10 to 24 carbon atoms. Examples thereof include behenyl neopentanoate, isononyl isonanonoate, isopropyl myristate and octyl stearate.

(b) Ether-esters such as fatty acid esters of ethoxylated saturated fatty alcohols.

(c) Polyhydric alcohol esters. Ethylene glycol mono and di-fatty acid esters, diethylene glycol mono- and di-fatty acid esters, polyethylene glycol (200-6000) mono- and di-fatty acid esters, propylene glycol mono- and di-fatty acid esters, polypropylene glycol 2000 monostearate, ethoxylated propylene glycol monostearate, glyceryl mono- and di-fatty acid esters, polyglycerol poly-fatty esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters are satisfactory polyhydric alcohol esters. Particularly useful are pentaerythritol, trimethylolpropane and neopentyl glycol esters of $C_1$-$C_{30}$ alcohols.

(d) Wax esters such as beeswax, spermaceti wax and tribehenin wax.

(e) Sugar ester of fatty acids such as sucrose polybehenate and sucrose polycottonseedate.

Natural ester emollients principally are based upon mono-, di- and tri-glycerides. Representative glycerides include sunflower seed oil, cottonseed oil, borage oil, borage seed oil, primrose oil, castor and hydrogenated castor oils, rice bran oil, soybean oil, olive oil, safflower oil, shea butter, jojoba oil and combinations thereof. Animal derived emollients are represented by lanolin oil and lanolin derivatives. Amounts of the natural esters may range from about 0.1 to about 20% by weight of the compositions.

Hydrocarbons which are suitable cosmetically acceptable carriers include petrolatum, mineral oil, $C_{11}$-$C_{13}$ isoparaffins, polybutenes, and especially isohexadecane, available commercially as Permethyl 101A from Presperse Inc.

Fatty acids having from 10 to 30 carbon atoms may also be suitable as cosmetically acceptable carriers. Illustrative of this category are pelargonic, lauric, myristic, palmitic, stearic, isostearic, oleic, linoleic, linolenic, hydroxystearic and behenic acids.

Surfactants may also be present in compositions of the present invention. Total concentration of the surfactant when present may range from about 0.1 to about 50%, preferably from about 1 to about 25%, optimally from about 1 to about 10% by weight of the composition, and being highly dependent upon the type of personal care product. The surfactant may be selected from the group consisting of anionic, nonionic, cationic and amphoteric actives. Particularly preferred nonionic surfactants are those with a $C_{10}$-$C_{20}$ fatty alcohol or acid hydrophobe condensed with from 2 to 100 moles of ethylene oxide or propylene oxide per mole of hydrophobe; $C_2$-$C_{10}$ alkyl phenols condensed with from 2 to 20 moles of alkylene oxide; mono- and di-fatty acid esters of ethylene glycol; fatty acid monoglyceride; sorbitan, mono- and di-$C_8$-$C_{20}$ fatty acids; and polyoxyethylene sorbitan as well as combinations thereof. Alkyl polyglycosides and saccharide fatty amides (e.g. methyl gluconamides) and trialkylamine oxides are also suitable nonionic surfactants.

Preferred anionic surfactants include soap, alkyl ether sulfates and sulfonates, alkyl sulfates and sulfonates, alkylbenzene sulfonates, alkyl and dialkyl sulfosuccinates, $C_8$-$C_{20}$ acyl isethionates, $C_8$-$C_{20}$ alkyl ether phosphates, $C_8$-$C_{20}$ sarcosinates, $C_8$-$C_{20}$ acyl lactylates, sulfoacetates and combinations thereof.

Useful amphoteric surfactants include cocoamidopropyl betaine, $C_{12}$-$C_{20}$ trialkyl betaines, sodium lauroamphoacetate, and sodium laurodiamphoacetate.

Adjunct humectants may be employed in the present invention. These are generally polyhydric alcohol-type materials. Typical polyhydric alcohols include glycerin, propylene glycol, dipropylene glycol, polypropylene glycol, polyethylene glycol, sorbitol, hydroxypropyl sorbitol, hexylene glycol, 1,3-butylene glycol, isoprene glycol, 1,2,6-hexanetriol, ethoxylated glycerol, propoxylated glycerol and mixtures thereof. The amount of adjunct humectant may range anywhere from about 0.2 to about 40%, preferably between 1 and 25%, most preferably between 2 and 15% by weight of the composition. Most preferred is glycerin as an adjunct humectant or moisturizer.

Sunscreen agents may also be included in compositions of the present invention. Particularly preferred are such materials as ethylhexyl p-methoxycinnamate, available as Parsol MCX®, Avobenzene available as Parsol 1789®, and benzophenone-3 also known as Oxybenzone. Inorganic sunscreen actives may be employed such as microfine (1 to 100 nm) titanium dioxide and zinc oxide. Amounts of the sunscreen agents when present may generally range from 0.1 to 30%, preferably from 2 to 20%, optimally from 4 to 10% by weight of the composition.

Antiperspirants and deodorant compositions of the present invention ordinarily will contain astringent actives. Examples include aluminum chloride, aluminum chlorhydrex, aluminum-zirconium chlorhydrex glycine, aluminum sulfate, zinc sulfate, zirconium and aluminum chlorohydroglycinate, zirconium hydroxychloride, zirconium and aluminum lactate, zinc phenolsulfonate and combinations thereof. Amounts of the astringents may range anywhere from about 0.5 to about 50% by weight of the composition.

Dental products formulated according to the present invention will generally contain a fluoride source to prevent dental caries. Typical anti-caries actives include sodium fluoride, stannous fluoride and sodium monofluoro phosphate. Amounts of these materials will be determined by the amount of fluoride releasable which should range between about 500 to about 8800 ppm of the composition. Other components of dentifrices can include desensitizing agents such as potassium nitrate and strontium nitrate, sweeteners such as sodium saccharine, aspartame, sucralose, and potassium acesulfam. Thickeners, opacifying agents, abrasives and colorants will normally also be present.

Preservatives can desirably be incorporated into the personal care compositions of this invention to protect against the growth of potentially harmful microorganisms. Particularly preferred preservatives are phenoxyethanol, methyl paraben, propyl paraben, imidazolidinyl urea, dimethyloldimethylhydantoin, ethylenediaminetetraacetic acid salts (EDTA), sodium dehydroacetate, methylchloroisothiazolinone, methylisothiazolinone, iodopropynbutylcarbamate and benzyl alcohol. The preservatives should be selected having regard for the use of the composition and possible incompatibilities between the preservatives and other ingredients. Preservatives are preferably employed in amounts ranging from 0.0001% to 2% by weight of the composition.

Compositions of the present invention may include vitamins. Illustrative vitamins are Vitamin A (retinol), Vitamin $B_2$, Vitamin $B_3$ (niacinamide), Vitamin $B_6$, Vitamin C, Vitamin E, Folic Acid and Biotin. Derivatives of the vitamins may also be employed. For instance, Vitamin C derivatives include ascorbyl tetraisopalmitate, magnesium ascorbyl phosphate and ascorbyl glycoside. Derivatives of Vitamin E include tocopheryl acetate, tocopheryl palmitate and tocopheryl linoleate. DL-panthenol and derivatives may also be employed. Total amount of vitamins when present in compositions according to the present invention may range from 0.001 to 10%, preferably from 0.01% to 1%, optimally from 0.1 to 0.5% by weight of the composition.

Another type of useful substance can be that of an enzyme such as amylases, oxidases, proteases, lipases, cellulases, elastases and combinations.

Skin lightening compounds may be included in the compositions of the invention. Illustrative substances are placental extract, lactic acid, niacinamide, arbutin, kojic acid, ferulic acid, resorcinol and derivatives including 4-substituted resorcinols and combinations thereof. Amounts of these agents may range from about 0.1 to about 10%, preferably from about 0.5 to about 2% by weight of the composition.

Desquamation promoters may be present. Illustrative are the alpha-hydroxycarboxylic acids and beta-hydroxycarboxylic acids. The term "acid" is meant to include not only the free acid but also salts and $C_1$-$C_{30}$ alkyl or aryl esters thereof and lactones generated from removal of water to form cyclic or linear lactone structures. Representative acids are glycolic, lactic and malic acids. Salicylic acid is representative of the beta-hydroxycarboxylic acids. Amounts of these materials when present may range from about 0.01 to about 15% by weight of the composition.

A variety of herbal extracts may optionally be included in compositions of this invention. The extracts may either be water soluble or water-insoluble carried in a solvent which respectively is hydrophilic or hydrophobic. Water and ethanol are the preferred extract solvents. Illustrative extracts include those from green tea, chamomile, licorice, aloe vera, grape seed, citrus unshui, willow bark, sage, thyme and rosemary.

Also included may be such materials as lipoic acid, retinoxytrimethylsilane (available from Clariant Corp. under the Silcare 1 M-75 trademark), dehydroepiandrosterone (DHEA) and combinations thereof. Ceramides (including Ceramide 1, Ceramide 3, Ceramide 3B and Ceramide 6) as well as pseudoceramides may also be useful. Amounts of these materials may range from about 0.000001 to about 10%, preferably from about 0.0001 to about 1% by weight of the composition.

Colorants, opacifiers and abrasives may also be included in compositions of the present invention. Each of these substances may range from about 0.05 to about 5%, preferably between 0.1 and 3% by weight of the composition.

Personal care compositions of the present invention may be in any form. These forms may include lotions, creams, roll-on formulations, sticks, mousses, aerosol and non-aerosol sprays and fabric (e.g. nonwoven textile)-applied formulations.

A wide variety of packaging can be employed to store and deliver the personal care compositions. Packaging is often dependent upon the type of personal care end-use. For instance, leave-on skin lotions and creams, shampoos, hair conditioners and shower gels generally employ plastic containers with an opening at a dispensing end covered by a closure. Typical closures are screw-caps, non-aerosol pumps and flip-top hinged lids. Packaging for antiperspirants, deodorants and depilatories may involve a container with a roll-on ball on a dispensing end. Alternatively these types of personal care products may be delivered as a stick composition formulation in a container with propel-repel mechanism where the stick moves on a platform towards a dispensing orifice. Metallic cans pressurized by a propellant and having a spray nozzle serve as packaging for antiperspirants, shave creams and other sprayable personal care products. Toilet bars may have packaging constituted by a cellulosic or plastic wrapper or within a cardboard box or even encompassed by a shrink wrap plastic film.

Another aspect of compositions of this invention may be the inclusion of instructions attached to or otherwise associated with the packaging. The instructions indicate to a consumer topical use of the composition on skin, hair or oral mucosae. Packaging itself will usually be printed with the instructions but sometimes a separate written insert within the package may serve to provide the instructions. Typical language includes phrases such as "apply a thin layer to the underarm", "apply regularly to hands", "apply to wet hair, lather and rinse", "cleanse skin" and "pump a small amount onto the palm of your hand".

The term "comprising" is meant not to be limiting to any subsequently stated elements but rather to encompass non-specified elements of major or minor functional importance. In other words the listed steps, elements or options need not be exhaustive. Whenever the words "including" or "having" are used, these terms are meant to be equivalent to "comprising" as defined above.

Except in the operating and comparative examples, or where otherwise explicitly indicated, all numbers in this description indicating amounts of material ought to be understood as modified by the word "about".

All documents referred to herein, including all patents, patent applications, and printed publications, are hereby incorporated by reference in their entirety in this disclosure.

The following examples will more fully illustrate the embodiments of this invention. All parts, percentages and proportions referred to herein and in the appended claims are by weight unless otherwise illustrated.

EXAMPLE 1

A representative personal care composition of the present invention in the form of a cosmetic lotion is outlined under Table I.

TABLE I

| INGREDIENT | WEIGHT % |
|---|---|
| PHASE A | |
| Water | Balance |
| Disodium EDTA | 0.05 |
| Methyl Paraben | 0.15 |
| Magnesium Aluminum Silicate | 0.60 |
| Triethanolamine | 1.20 |
| Dihydroxypropyltrimonium Chloride | 5.00 |
| PHASE B | |
| Xanthan Gum | 0.20 |
| Natrosol ® 250HHR (ethyl cellulose) | 0.50 |
| Butylene Glycol | 3.00 |
| Glycerin | 10.00 |
| PHASE C | |
| Sodium Stearoyl Lactylate | 0.10 |
| Glycerol Monostearate | 1.50 |
| Stearyl Alcohol | 1.50 |
| Isostearyl Palmitate | 3.00 |
| Silicone Fluid | 1.00 |
| Cholesterol | 0.25 |
| Sorbitan Stearate | 1.00 |
| Butylated Hydroxy Toluene | 0.05 |
| Vitamin E Acetate | 0.01 |
| PEG-100 Stearate | 2.00 |
| Stearic Acid | 3.00 |
| Propyl Paraben | 0.10 |
| Parsol MCX ® | 2.00 |
| Caprylic/Capric Triglyceride | 0.50 |
| Hydroxycaprylic Acid | 0.01 |
| C12-15 Alkyl Octanoate | 3.00 |
| PHASE D | |
| Vitamin A Palmitate | 0.10 |
| Bisabolol | 0.01 |
| Vitamin A Acetate | 0.01 |
| Fragrance | 0.03 |
| Retinol 50C | 0.02 |
| Conjugated Linoleic Acid | 0.50 |

EXAMPLE 2

A water-in-oil topical liquid make-up foundation according to the present invention is described in Table II below.

TABLE II

| INGREDIENT | WEIGHT % |
|---|---|
| PHASE A | |
| Cyclomethicone | 9.25 |
| Oleyl Oleate | 2.00 |
| Dimethicone Copolyol | 20.00 |
| PHASE B | |
| Talc | 3.38 |
| Pigment (Iron Oxides) | 10.51 |
| Spheron L-1500 (Silica) | 0.50 |
| PHASE C | |
| Synthetic Wax Durachem 0602 | 0.10 |

TABLE II-continued

| INGREDIENT | WEIGHT % |
|---|---|
| Arachidyl Behenate | 0.30 |
| PHASE D | |
| Cyclomethicone | 1.00 |
| Trihydroxystearin | 0.30 |
| PHASE E | |
| Laureth-7 | 0.50 |
| Propyl Paraben | 0.25 |
| PHASE F | |
| Fragrance | 0.05 |
| PHASE G | |
| Water | balance |
| Dihydroxypropyltrimonium Chloride | 4.00 |
| Methyl Paraben | 0.12 |
| Propylene Glycol | 8.00 |
| Niacinamide | 4.00 |
| Glycerin | 12.00 |
| Sodium Chloride | 2.00 |
| Sodium Dehydroacetate | 0.30 |

EXAMPLE 3

Illustrated herein is a skin cream incorporating a quat salt and silicone of the present invention.

TABLE III

| INGREDIENT | WEIGHT % |
|---|---|
| Glycerin | 15.00 |
| Niacinamide | 5.00 |
| Dihydroxypropyltrimonium Chloride | 5.00 |
| Permethyl 101A[1] | 3.00 |
| Sepigel 305[2] | 2.50 |
| Q2-1403[3] | 2.00 |
| Linseed Oil | 1.33 |
| Arlatone 2121[4] | 1.00 |
| Cetyl Alcohol CO-1695 | 0.72 |
| SEFA Cottonate[5] | 0.67 |
| Tocopherol Acetate | 0.50 |
| Panthenol | 0.50 |
| Stearyl Alcohol | 0.48 |
| Titanium Dioxide | 0.40 |
| Disodium EDTA | 0.10 |
| Glydant Plus[6] | 0.10 |
| PEG-100 Stearate | 0.10 |
| Stearic Acid | 0.10 |
| Purified Water | Balance |

[1] Isohexadecane, Presperse Inc., South Plainfield, NJ
[2] Polyacrylamide(and)C13-14 Isoparaffin(and) Laureth-7, Seppic Corporation, Fairfield, NJ
[3] dimethicone(and)dimethiconol, Dow Corning Corp. Midland, MI
[4] Sorbitan Monostearate and Sucrococoate, ICI Americas Inc., Wilmington, DE
[5] Sucrose ester of fatty acid
[6] DMDM Hydantoin (and) Iodopropynyl Butylcarbamate, Lonza Inc., Fairlawn, NJ

EXAMPLE 4

Illustrative of another cosmetic composition incorporating the quat salt and a silicone according to the present invention is the formula of Table IV.

TABLE IV

| INGREDIENT | WEIGHT % |
| --- | --- |
| Polysilicone-11 | 29 |
| Cyclomethicone | 59 |
| Glycerin | 10 |
| Dihydroxypropyltrimonium Chloride | 1.2 |
| Dimethicone Copolyol | 0.5 |
| Sunflowerseed Oil | 0.3 |

EXAMPLE 5

A relatively anhydrous composition incorporating the quat salt and a silicone of the present invention is reported in Table V.

TABLE V

| INGREDIENT | WEIGHT % |
| --- | --- |
| Cyclomethicone | 60.65 |
| Glycerin | 15.00 |
| Dimethicone | 10.10 |
| Squalane | 6.00 |
| Dihydroxypropyltrimonium Chloride | 5.00 |
| Isostearic Acid | 1.90 |
| Borage Seed Oil | 0.90 |
| Retinyl Palmitate | 0.25 |
| Ceramide 6 | 0.10 |
| Tocopherol | 0.10 |

EXAMPLE 6

An aerosol packaged foaming cleanser with a quat salt and silicone suitable for the present invention is outlined in Table VI.

TABLE VI

| INGREDIENT | WEIGHT % |
| --- | --- |
| Sunflower Seed Oil | 10.00 |
| Glycerin | 10.00 |
| Maleated Soybean Oil | 5.00 |
| Silicone Urethane | 1.00 |
| Polyglycero-4 Oleate | 1.00 |
| Sodium C14-16 Olefin Sulfonate | 15.00 |
| Sodium Lauryl Ether Sulphate 25% active | 15.00 |
| Cocoamidopropylbetaine | 15.00 |
| DC 1784 ® (Silicone Emulsion 50%) | 5.00 |
| Polyquaternium-11 | 1.00 |
| Dihydroxypropyltrimonium Chloride | 1.00 |
| Water | Balance |

EXAMPLE 7

A disposable, single use personal care towelette product is described according to the present invention. A 70/30 polyester/rayon non-woven towelette is prepared with a weight of 1.8 grams and dimensions of 15 cm by 20 cm. Onto this towelette is impregnated 1.0 grams of a composition including a quaternary ammonium salt and a silicone microemulsion as outlined in Table VII below.

TABLE VII

| INGREDIENT | WEIGHT % |
| --- | --- |
| Dihydroxypropyltrimonium Chloride | 4.00 |
| Glycerin | 12.00 |
| Hexylene Glycol | 2.00 |
| Disodium Capryl Amphodiacetate | 1.00 |
| Gluconolactone | 0.90 |
| Silicone Microemulsion | 0.85 |
| Witch Hazel | 0.50 |
| PEG-40 Hydrogenated Castor Oil | 0.50 |
| Fragrance | 0.20 |
| Vitamin E Acetate | 0.001 |
| Water | Balance |

EXAMPLE 8

A toilet bar illustrative of the present invention is outlined under Table VII.

TABLE VIII

| INGREDIENT | WEIGHT % |
| --- | --- |
| Sodium Soap (85/15 Tallow/Coconut) | 77.77 |
| Dihydroxypropyltrimonium Chloride | 3.50 |
| Dimethicone | 2.00 |
| Sodium Chloride | 0.77 |
| Titanium Dioxide | 0.40 |
| Fragrance | 1.50 |
| Disodium EDTA | 0.02 |
| Sodium Etidronate | 0.02 |
| Fluorescer | 0.024 |
| Water | Balance |

EXAMPLE 9

A shampoo composition useful in the context of the present invention is described in Table IX below.

TABLE IX

| Ingredient | Weight % |
| --- | --- |
| Ammonium Laureth Sulfate | 12.00 |
| Ammonium Lauryl Sulfate | 2.00 |
| Cocoamidopropyl Betaine | 2.00 |
| Sodium Lauroamphoacetate | 2.00 |
| Glycerin | 12.00 |
| Dihydroxypropyltrimonium Chloride | 5.50 |
| Ethylene Glycol Distearate | 1.50 |
| Cocomonoethanolamide | 0.80 |
| Cetyl Alcohol | 0.60 |
| Polyquaternium-10 | 0.50 |
| Dimethicone | 1.00 |
| Zinc Pyridinethione | 1.00 |
| Sodium Citrate | 0.40 |
| Citric Acid | 0.39 |
| Sodium Xylene Sulfonate | 1.00 |
| Fragrance | 0.40 |
| Sodium Benzoate | 0.25 |
| Kathon CG ® | 0.0008 |
| Benzyl Alcohol | 0.0225 |
| Water | Balance |

EXAMPLE 10

This Example illustrates an antiperspirant/deodorant formula incorporating the quat salts and silicones according to the present invention.

TABLE X

| Ingredient | Weight % |
| --- | --- |
| Cyclopentasiloxane | 39 |
| Dimethicone | 20 |
| Aluminum Zirconium Trichlorohydrex Glycinate | 15 |
| Dihydroxypropyltrimonium Chloride | 5.0 |
| $C_{18}$-$C_{36}$ Acid Triglyceride | 5.0 |
| Microcrystalline Wax | 3.0 |
| Glycerin | 8.0 |
| Silica | 2.5 |
| Dimethicone Crosspolymer | 1.0 |
| Fragrance | 0.5 |
| Disodium EDTA | 0.4 |
| Butylated Hydroxytoluene | 0.3 |
| Citric Acid | 0.3 |

EXAMPLE 11

A toothpaste according to the present invention can be formulated with the ingredients listed under Table XI.

TABLE XI

| Ingredients | Weight % |
| --- | --- |
| Zeodent 115 ® | 20.00 |
| Glycerin | 18.00 |
| Xanthan Gum | 7.00 |
| Sodium Carboxymethyl Cellulose | 0.50 |
| Sodium Bicarbonate | 2.50 |
| Dihydroxypropyltrimonium Chloride | 2.00 |
| Sodium Laurylsulfate | 1.50 |
| Sodium Fluoride | 1.10 |
| Sodium Saccharin | 0.40 |
| Titanium Dioxide | 1.00 |
| Pluronic F-127 ® | 2.00 |
| FD&C Blue No. 1 | 3.30 |
| Menthol | 0.80 |
| PEG-10 Dimethicone | 0.50 |
| Water | balance |

EXAMPLE 12

This Example details the synthesis of 2,3-dihydroxypropyl trimethylammonium chloride (identified in Table XII as dihydroxypropyl trimonium chloride). A 125 ml erlenmeyer flask was charged with 16.7 ml (53 mmol) of 3-chloro-2-hydroxypropyl trimethylammonium chloride (employed as a 60% material in water as Quat 188®). The flask was equipped with a dropping funnel and stirring bar. A solution of sodium hydroxide (55 ml, 55.0 mmol) was charged into the flask via the dropping funnel at a rate to maintain room temperature of the reaction. Once addition was complete, the solution was stirred under ambient conditions for about 12 hours, followed by heating at 50° C. for two hours.

Progress of the reaction was monitored by thin layer chromatography (TLC). Product was spotted on a 2.5 by 7.6 cm silica gel plate alongside the starting material and eluted with butanol:acetic acid:water (4:2:2) for approximately 50 minutes. Visualization was executed with ninhydrin stain and scorching on a hotplate.

Crude product solution was first acidified to pH of 7, and then concentrated to remove water. Ethanol (200 ml) was added to the crude product with stirring. Upon sitting, sodium chloride precipitated and was filtered off under vacuum. The filtrate was concentrated under vacuum on a Rotavap®, followed by additional drying under high vacuum (0.05 mmHg).

A cloudy gel was obtained yielding the final product in 97% yield. TLC analysis indicated a major spot at $R_f$=0.27.

A 60 MHz proton NMR ($D_2O$ w/TSP) was run on the final product. The spectra confirmed the final product structure. Mass Spectrum analysis in positive ion mode revealed a $M^+$ of 134 (minus chlorine).

EXAMPLE 13

A series of experiments were conducted to evaluate skin-feel performance through instrumentation. A series of samples 1 through 5c were prepared for evaluation in a stick/slip friction test. Base formula for all of the samples was a 20% aqueous glycerin solution thickened with 2% Carbopol 980® into which varying amounts of dihydroxypropyltrimonium chloride and dimethicone (DC 200/50) were blended.

Measurement of Stick or Tack

A measured amount of each sample (200 microliters) was applied to a one-inch diameter layer of closed cell neoprene mounted on a stainless steel plate. The plate was mounted on the crosshead of an Instron Model 4501 Universal Testing Instrument (Instron Corp., Canton, Mass.). Another one-inch diameter layer of closed cell neoprene was attached to a stainless steel plate, which was mounted to a compression load cell on the Instron's Load Frame. The two layers were compressed at a rate of 10 cm/min to a compression force of 100 grams and then separated at a rate of 10 cm/min. The force of separation is defined as Stick or Tack and is measured in grams. Each sample was run five times.

Measurement of Sliding Friction

An excess amount of each sample was applied to a glass and drawn down to a film of 75 microns thick, 6 inches long and 0.5 inches wide using a drawdown knife. The plate was mounted on the crosshead of an Instron Model 4501 Universal Testing Instrument. An aluminum sled measuring 7.6 cm by 2.5 cm and weighing 19 grams was attached to the Instron's Load Cell. After allowing the film to dry for one minute the sled was pulled across the surface at 10 cm/min. The average amount of work is defined as Sliding Friction and is measured in gram-cm.

TABLE XII

| Sample No. | Glycerol Quat (%) | Dimethicone (%) | Stick (Tack, g) | Friction g-cm |
| --- | --- | --- | --- | --- |
| 1 | 0.0 | 0.0 | 67.0 | 2081 |
| 2 | 0.1 | 0.0 | 37.3 | 1394 |
| 3a | 0.0 | 0.1 | 66.4 | 2243 |
| 3b | 0.0 | 0.5 | 66.5 | 2396 |
| 3c | 0.0 | 1.0 | 67.0 | 2756 |
| 4a | 0.1 | 0.1 | 37.6 | 1783 |
| 4b | 0.1 | 0.5 | 41.9 | 2016 |
| 4c | 0.1 | 1.0 | 46.6 | 2341 |
| 4ai | 0.2 | 0.2 | 35.6 | 1777 |
| 4bi | 0.2 | 1.0 | 44.5 | 1966 |
| 4ci | 0.2 | 2.0 | 46.4 | 2443 |
| 4aii | 1.0 | 1.0 | 39.3 | 1953 |
| 4bii | 1.0 | 5.0 | 45.1 | 2274 |
| 4cii | 1.0 | 10.0 | 45.5 | 2563 |
| 5a | 5.0 | 0.0 | 34.5 | 2189 |
| 5b | 5.0 | 1.0 | 40.7 | 1470 |
| 5c | 10.0 | 1.0 | 40.9 | 1272 |

Higher numbers for "tack" indicate greater stickiness of the sample. Higher "friction" values relate to increased dry. Thus, lower values for tack and friction indicate better aspects of skinfeel.

Samples 3a through 3c are formulated with dimethicone. These formulas all have relatively high stick and friction values. Samples 4a through 5c demonstrate that addition of dihydroxypropyltrimonium chloride (glycerol quat) has a significantly positive effect upon reducing tack and friction of the formulas.

What is claimed is:

1. A personal care composition comprising:
   (i) from about 0.05% to about 30% by weight of a dihydroxypropyl quaternary ammonium salt of structure AB, wherein
      A is a cationic charged component of the salt AB,
      B is an anionic charged component of the salt AB, and
      A has a single quaternized nitrogen atom, at least two hydroxy groups and a molecular weight no higher than about 250;
   (ii) from about 0.05 to about 50% by weight of a silicone.

2. The composition according to claim 1 wherein the quaternary ammonium salt is a dihydroxypropyltri($C_1$-$C_3$ alkyl) ammonium salt.

3. The composition according to claim 2 wherein the salt is dihydroxypropyltrimonium chloride.

4. The composition according to claim 1 which is selected from the group consisting of leave-on skin lotions and creams, shampoos, hair conditioners, shower gels, toilette bars, antiperspirants, deodorants, dental products, shave creams, depilatories, lipsticks, foundations, mascara, sunless tanner and sunscreen lotions.

5. The composition according to claim 1 wherein the silicone is a cyclomethicone.

6. The composition according to claim 1 wherein the silicone is dimethicone.

7. The composition according to claim 1 wherein the silicone is a dimethicone/vinyl dimethicone crosspolymer.

8. A method for moisturizing human body parts while still providing an aesthetically pleasing skinfeel comprising topically applying to the human body parts a personal care composition comprising from about 0.05 to about 30% by weight of a quaternary ammonium salt which is a salt of structure AB wherein
   A is a cationic charged component of the salt AB
   B is an anionic charged component of the salt AB, and
   A has a single quaternized nitrogen atom, at least two hydroxy groups and a molecular weight no higher than about 250; and
from about 0.05 to about 50% of silicone by weight of the composition.

\* \* \* \* \*